United States Patent [19]
Takahashi et al.

[11] Patent Number: 6,048,444
[45] Date of Patent: Apr. 11, 2000

[54] CAPILLARY ELECTROPHORESIS APPARATUS

[75] Inventors: Satoshi Takahashi, Kunitachi; Hideki Kambara, Hachiouji; Takashi Yamada, Setagaya-ku, all of Japan

[73] Assignee: Hitachi, Ltd., Tokyo, Japan

[21] Appl. No.: 08/979,542

[22] Filed: Nov. 26, 1997

[30] Foreign Application Priority Data

Nov. 28, 1996 [JP] Japan ................. 8-317436

[51] Int. Cl.$^7$ .......... G01N 27/26; G01N 27/447
[52] U.S. Cl. .......... 204/603; 204/451; 204/452; 204/601; 422/81; 422/82.05; 422/82.07; 422/102
[58] Field of Search .................. 204/451, 452, 204/453, 454, 455, 601, 602, 603, 604, 605; 422/81, 102, 82.05, 82.07

[56] References Cited

U.S. PATENT DOCUMENTS

| | | | |
|---|---|---|---|
| 4,830,830 | 5/1989 | Tamotu et al. | 204/605 |
| 5,439,578 | 8/1995 | Dovichi et al. | 204/603 |
| 5,529,679 | 6/1996 | Takahashi et al. | 204/603 |
| 5,582,705 | 12/1996 | Yeung et al. | 204/605 X |

FOREIGN PATENT DOCUMENTS 6-138037  5/1994  Japan .

OTHER PUBLICATIONS

"Analytical Biochemistry", 215, pp. 163–170, 1993.

Y. Baba, "A Grounding in Chromatography—Capillary Electrophoresis", *Bunseki 1995*, No. 5, pp. 342–349, 1995, Japan Society for Analytical Chemistry (in Japanese), No month available.

*Primary Examiner*—Jill Warden
*Assistant Examiner*—John S. Starsiak, Jr.
*Attorney, Agent, or Firm*—Antonelli, Terry, Stout & Kraus, LLP

[57] ABSTRACT

A capillary electrophoresis apparatus of the invention has: a plurality of capillaries which are filled with a migration medium and have first ends into which samples are injected and second ends in which components included in the samples are eluted; a sheath flow cell in which the second ends are arranged in a straight line at first predetermined intervals and are terminated and a sheath flow is formed; a buffer solution vessel for housing a buffer solution flowing in the sheath flow cell; a drain vessel housing the buffer solution flowed from the sheath flow cell; an optical system emitting laser light to a part near the second ends; and a fluorescent detection system for detecting fluorescent light generated from fluorophore labelling the components included in the sample eluted near the second ends by the emission of laser light, wherein the buffer solution flows from the lower part to the upper part of the sheath flow cell, thereby forming a sheath flow in the sheath flow cell.

19 Claims, 5 Drawing Sheets

CAPILLARY ELECTROPHORESIS APPARATUS

BACKGROUND OF THE INVENTION

The present invention relates to a capillary electrophoresis apparatus for separating and analyzing DNA, protein, and the like.

Techniques of analyzing DNA, protein, and the like are important in the medical and biological fields including gene analysis and gene diagnosis. A DNA analyzing apparatus having high throughput is being developed recently. Those analyses are mainly performed by a gel electrophoresis. In the gel electrophoresis, a substance in a gel state is used as a separating medium of the electrophoresis, DNA labelled with fluorophore is usually prepared and the fluorescence labelled DNA sample is injected into the upper end of polyacrylamide gel formed between two glass plates (slab gel). After that, an electrical field is applied to both ends of the gel, components (fragments) of the sample DNA are allowed to migrate to the lower end, a predetermined position from the upper end is irradiated with laser light, and fluorophore is detected. The result is analyzed, and DNA base sequence is determined or polymorphism of a restriction fragment is identified. Recently, in place of the slab gel, a capillary gel obtained by polymerizing gel in a capillary is often used. Attention is paid to a capillary electrophoresis as a method which enables high speed and high separation since an electric field larger than that used in the slab gel electrophoresis can be applied. In a capillary electrophoresis apparatus, on-column measurement in which one capillary column is used, capillaries near the lower end are irradiated with laser light, and the fluorophore is detected, is usually used ("Bunseki", 1995, No. 5, pp. 342–349).

A capillary array gel electrophoresis apparatus for simultaneously analyzing a number of samples by using a plurality of capillaries in order to improve the throughput has been reported. According to a first example, on-column fluorescent measurement is performed in such a manner that a plurality of capillaries are arranged on a moving stage and the moving stage is moved, thereby sequentially irradiating the capillaries one by one with laser light ("Analytical Biochemistry", 215, pp. 163 to 170, 1993). A second example relates to a method of using a sheath flow (Japanese Patent Application Laid-Open No. 06-138037 and U.S. Pat. No. 5,529,679). In an apparatus according to the second example, the lower end of a capillary array is soaked in a buffer solution, components of the sample separated by the gel electrophoresis are eluted in the buffer solution, and fluorescent light from the sample component is detected in a part where no capillary exists.

SUMMARY OF THE INVENTION

In a capillary gel electrophoresis, both ends of a capillary are directly soaked into an electrolyte solution in an electrode vessel (positive electrode and negative electrode) and a voltage is applied. Similarly, when a sample to be measured is injected into a capillary gel, a vessel such as a sample tube is filled with a measurement sample solution and one end of the capillary is directly soaked into the measurement sample solution, and a voltage is applied across the one end and the other end. That is, the sample injecting end of the capillary is arranged almost vertically above the electrolyte solution in the electrode vessel or the measurement sample solution in the sample vessel and is almost vertically inserted. Similarly, the capillary is bent in the middle, and the other end of the capillary is arranged so as to be almost vertically inserted into the electrolyte solution in the electrode vessel. With respect to the moving direction of the sample to be measured in the capillary, it is moved vertically upward at the injecting end of the capillary and it is contrarily moved vertically downward at the other end of the capillary, so that the moving directions are opposite. With such arrangement, the capillary itself serves as a pipet, so that the sample solution can be easily injected into the capillary. Since the capillary is bent, however, a certain length of the capillary which can be used is necessary. For example, it is difficult to make the total length of the capillary equal to or shorter than 20 cm, so that there is a problem that it is not suitable for high-speed electrophoresis.

When a plurality of capillaries are arranged and used, the group of capillaries cannot help but be arranged in a three-dimensional space and air has to be circulated in order to adjust the temperature of the group of capillaries, so that there is a problem that the structure of the apparatus is enlarged. Further, by bending the capillary, there is the possibility that the separating performance deteriorates. The capillary is generally covered by brown-colored polyimide which emits fluorescent light at the time of fluorescent detection or the like in which Argon laser light or the like is used as excitation light. The emitted fluorescent light becomes background light, so that there is a problem that measurement sensitivity tends to deteriorate. Further, in a capillary array apparatus using sheath flow, there is the possibility that dusts or bubbles in the buffer solution become noises, so that it is necessary to pay attention at the time of installation and measurement.

It is an object of the invention to provide a high-speed and high-precision capillary electrophoresis apparatus which solves the above problems and in which operations of the temperature adjustment and sample injection are easy.

The object can be achieved by keeping the direction of the sample injecting end of each capillary almost vertically and arranging a plurality of capillaries without bending or bending back. That is, it is arranged in such a manner that the position of a sample detection point is set higher than a sample injecting end, the sample injecting end is directed vertically downward, and the sample detection point is directed vertically upward or almost horizontally. With such a construction, a single capillary or a plurality of capillaries can be arranged without being bent largely in the analysis region.

In an electrophoresis apparatus in which sample elution ends of a plurality of capillaries are arranged in a straight line in a sheath flow cell and are terminated and components eluted from the capillaries in the sheath flow cell are detected, the capillaries are arranged in a manner similar to the above. The termination faces of the sample elution ends of the capillaries are arranged near the lower part of the sheath flow cell so as to face the upper part of the cell, and a buffer solution flows from the lower part of the cell toward the upper part of the cell.

In a case of on-column detection, the detecting portion is placed upward of the sample injecting end and the capillaries from the injecting ends to the detecting points are arranged in a straight line.

Most parts in the longitudinal direction of the plurality of capillaries at least in an analyzing region are arranged almost in a vertical plane, the sample injection end of each capillary is arranged in the lower part and the sample is allowed to migrate upward to the detection portion, so that the migration direction of the sample is not reversed.

Further, by using black for the color of the coat at least near one end of each capillary, the background light is prevented from being generated from the capillary, so that high sensitive detection can be performed.

The features of the present invention will be described in further detail. According to the invention, a capillary electrophoresis apparatus comprises: a plurality of capillaries filled with migration media, having first ends into which samples are injected and second ends in which components included in the samples are eluted; a sheath flow cell in which the second ends are arranged in a straight line at first predetermined intervals and terminated; means for flowing a buffer solution from the lower part to the upper part of the sheath flow cell; and means for detecting components separated from the capillaries by electrophoresis near the second ends in the sheath flow cell, wherein the buffer solution flows from the lower part to the upper part in the sheath flow cell.

According to further characteristics of the invention, in the capillary electrophoresis apparatus, most parts of the capillaries are arranged almost in the same plane in the analysis region, a plurality of capillaries or rod members each having an outer shape of almost the same size as that of the capillary are arranged at the first predetermined intervals on both sides of an array of the second ends of the plurality of capillaries, the migration medium includes either gel or polymer, the first ends are arranged lower than the detecting positions or the second ends, a sample vessel having a plurality of wells which are arranged in a straight line at second predetermined intervals, at which the first ends are arranged, in parallel to the array of the first ends and house the plurality of samples, respectively, and means for moving the sample vessel.

Further, in a capillary electrophoresis apparatus using a plurality of capillaries each having a first end into which a sample is injected, a second end in which a component included in the sample is eluted, and a light irradiation part which is located between the first end and the second end and is irradiated with laser light, parts from the first ends to the light irradiation parts of the plurality of capillaries are arranged in the same plane, the first ends are arranged lower than the light irradiation parts, and the light irradiation part is irradiated with laser light in a direction parallel to the plane. According to the characteristics, since the plurality of capillaries are housed in a small space, the temperature can be controlled with a simple method and the plurality of capillaries can be held at almost the same temperature.

The present invention will be summarized as follows with reference to FIG. 1.

Both ends of each of a plurality of capillaries 90 are fixed to capillary holders 91 and 92, both of sample injecting ends 90a and sample elution ends 90b are cut so as to have the same length, and the sample elution ends 90b are attached together with the capillary holder 92 to the lower part of a sheath flow cell 83. In the capillary holder 92, dummy glass rods 93 are attached on both sides of each capillary 90 at the same intervals as those of the capillaries 90. A buffer solution flows in a path from a buffer solution vessel 80 via a tube 81, a holder 82 for holding the sheath flow cell, the sheath flow cell 83, a holder 84 for holding the sheath flow cell, and a tube 85 into a drain vessel 86. Sample components eluted from the capillary 90 are excited by a laser beam emitted to a position around the sample elution ends 90b and are detected by fluorescent substances. With such a structure, it is almost unnecessary to bend the capillaries and the most part of the capillary is arranged in the same plane.

In a case of on-column detection, the sample injecting points are placed below the detecting points and the capillaries in the analyzing region are arranged in a straight and in the same plane. According to the invention, a capillary electrophoresis in which operations such as temperature adjustment, sample injection, and the like are easy and high sensitive and prompt measurement can be performed can be realized.

DESCRIPTION OF THE PREFERRED EMBODIMENTS

First Embodiment

An apparatus and method for using a plurality of capillaries (that is, a capillary array) filled with gel and the determining DNA base sequence will be described hereinbelow. DNA sequencing samples (DNA fragments labelled with fluorophore (fluorophore labelled DNA fragment)) are prepared. Primers labelled with fluorophores in which the maximum fluorescent wavelengths are about 550 nm, about 520 nm, 575 nm, and 605 nm (called FA, FC, FG, and FT, respectively) are used for fragment groups of A, C, G, and T, respectively. The fluorophore labelled DNA fragments are prepared by using these labelled primers according to a known dideoxy chain termination method by Sanger et al. These four fragment groups are finally mixed in a single sample tube, and after ethanol precipation, eluted in de-ionized formamide (including tris buffer solution of $\frac{1}{10}$ quantity), thereby obtaining a sample solution. The sample solution is heated at 90° C. for two minutes to cause heat denaturation before injection into a gel capillary, and after that, immediately cooled with ice, and injected into the sample injection end of the capillary. The sample can be also prepared by labelling a terminator, not the primer, with the fluorophore.

Figure 1:
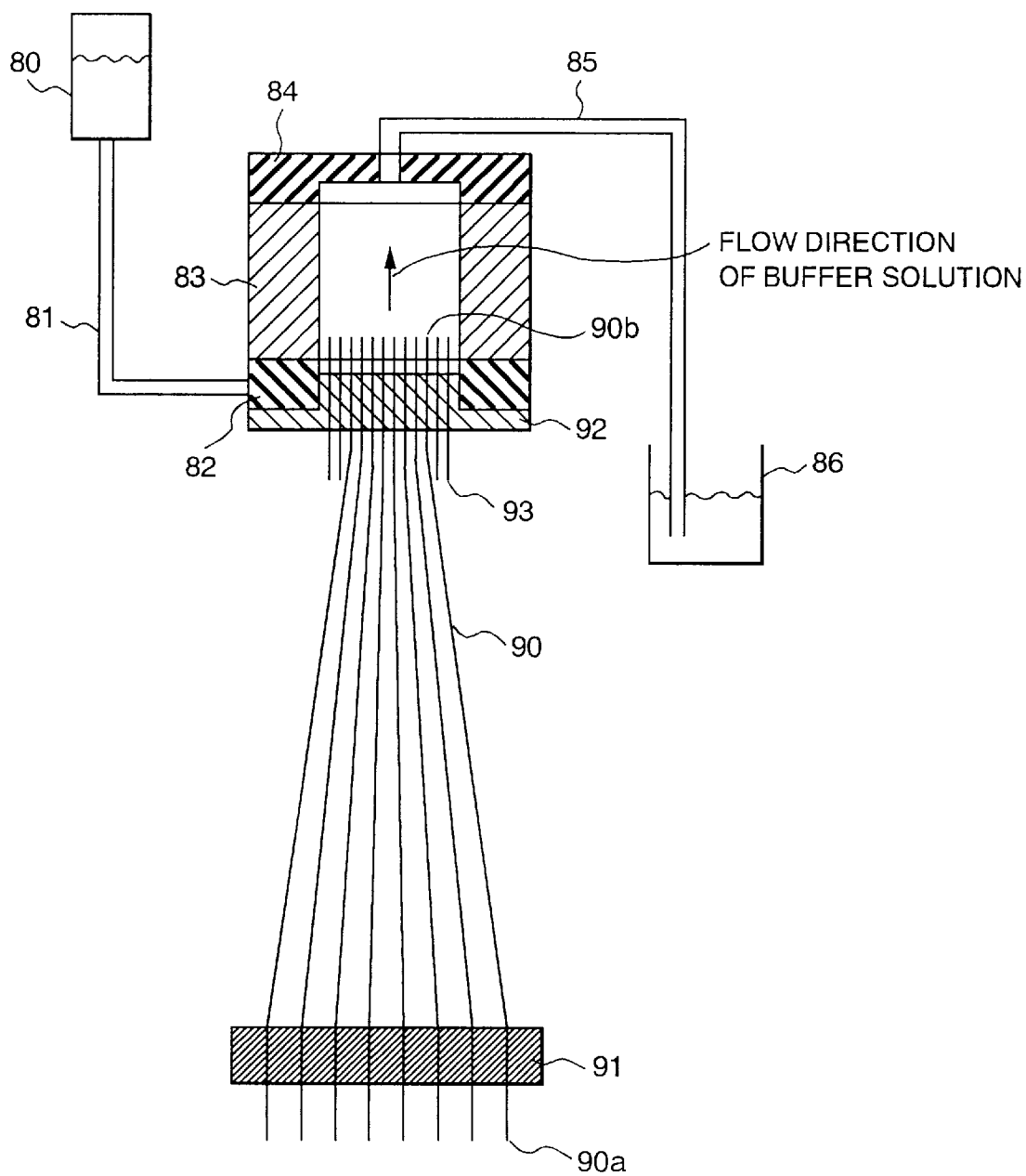
FIG. 1 is a diagram showing the construction and arrangement of a capillary array and a sheath flow cell serving as a fluorescent measurement unit according to a first embodiment of the invention.

The apparatus will be described hereinbelow. FIG. 1 is a diagram showing the construction and arrangement of a capillary array and a sheath flow cell serving as a fluorescence measuring part. A capillary array in which 48 capillaries filled with a gel are used (for simplicity, only a part of the capillaries is shown in the diagram and parts such as an O-ring for sealing the liquid and the like are omitted) and one ends of the capillaries are arranged in a straight line is produced. Although various inner and outer diameters can be used for the capillary, for example, capillaries each having the inner diameter of 0.075 mm, the outer diameter of 0.2 mm, and the length of about 20 cm are used. The capillaries are filled with polyacrylamide gel (gel concentration is 4% T (ratio of (acrylamide+bis-acrylamide) to the whole solution quantity and 5% C (ratio of the bis-acrylamide to (acrylamide+bis-acrylamide)) according to a known method and are used. Polymer gels such as hydroxyalkyl-cellulose, poly (vinyl alcohol) et al can be used as well.

Although polyimide is usually coated on the surface of the capillary in order to prevent damage when the capillary is bent or the like, the capillary which is coated in black by mixing carbon in polyimide or the like is used here. The black coating is performed at least near one (90b) of the ends of the capillary.

On the capillary holders 91 and 92, attaching grooves at intervals of 2.25 mm and at intervals of 0.4 mm are formed, respectively. Forty eight capillaries 90 are arranged on the same plane, both ends are fixed to the capillary holders 91 and 92, one ends of the capillaries are held at the intervals of 2.25 mm and the others are held at the intervals of 0.4 mm, and both ends of the capillaries are cut so as to be aligned, respectively. The capillary ends 90a fixed at the 2.25 mm intervals are ends on the sample injecting side and the capillary ends 90b on the other side are ends on the sample eluting side where separated sample fragments are eluted.

The capillary ends 90b are attached together with the capillary holder 92 to the lower part of the sheath flow cell 83. In the capillary holder 92, six pieces each of the dummy glass rods 93 are attached on both sides of the 48 capillaries 90 at the same intervals as those of the capillary ends 90b. The dummy glass rods 93 are provided so that environments of the capillary ends 90b of the capillaries 90 are uniformed. It is sufficient that the diameter of the dummy glass rod 93 is almost equal to that of the capillary 90. The capillary having the same diameter as that of the capillary 90 is used here and is filled with a solid matter. The number of dummy glass rods 93 depends on the width of the cross section of the passage of the sheath flow cell and is adjusted so that the capillaries are uniformly positioned in the whole width. By using the dummy glass rods 93, the environments of the sheath flow for the capillary ends 90b are uniformed and a uniform flow of the stable buffer solution can be formed near the capillary ends 90b of the first to the 48th capillaries 90.

The section of the passage of the sheath flow cell part is 0.22 mm×24.2 mm. The sheath flow cell part is constructed by the sheath flow cell 83 made of quartz glass and the holders 82 and 84 for holding the upper and lower parts of the sheath flow cell 83. The holders 82 and 84 have a space through which the buffer solution for sheath flows. A buffer solution equivalent to that obtained by preparing polyacrylamide gel is used as this buffer solution. The buffer solution flows from the buffer solution vessel 80, via the tube 81, the holder 82, the flow cell 83, the holder 84, and the tube 85 to the drain vessel 86. By arranging the buffer solution vessel 80 so as to be higher than the drain vessel 86, the buffer solution flows slowly and stably by the gravity, a laminate flow is formed, and a sheath flow is formed near the capillary ends 90b. That is, the buffer solution vessel 80 and the drain vessel 86 are arranged so that the liquid level of the buffer solution vessel 80 is higher than that of the drain vessel 86 and the stable flow of the buffer solution by gravity is formed.

Figure 2:
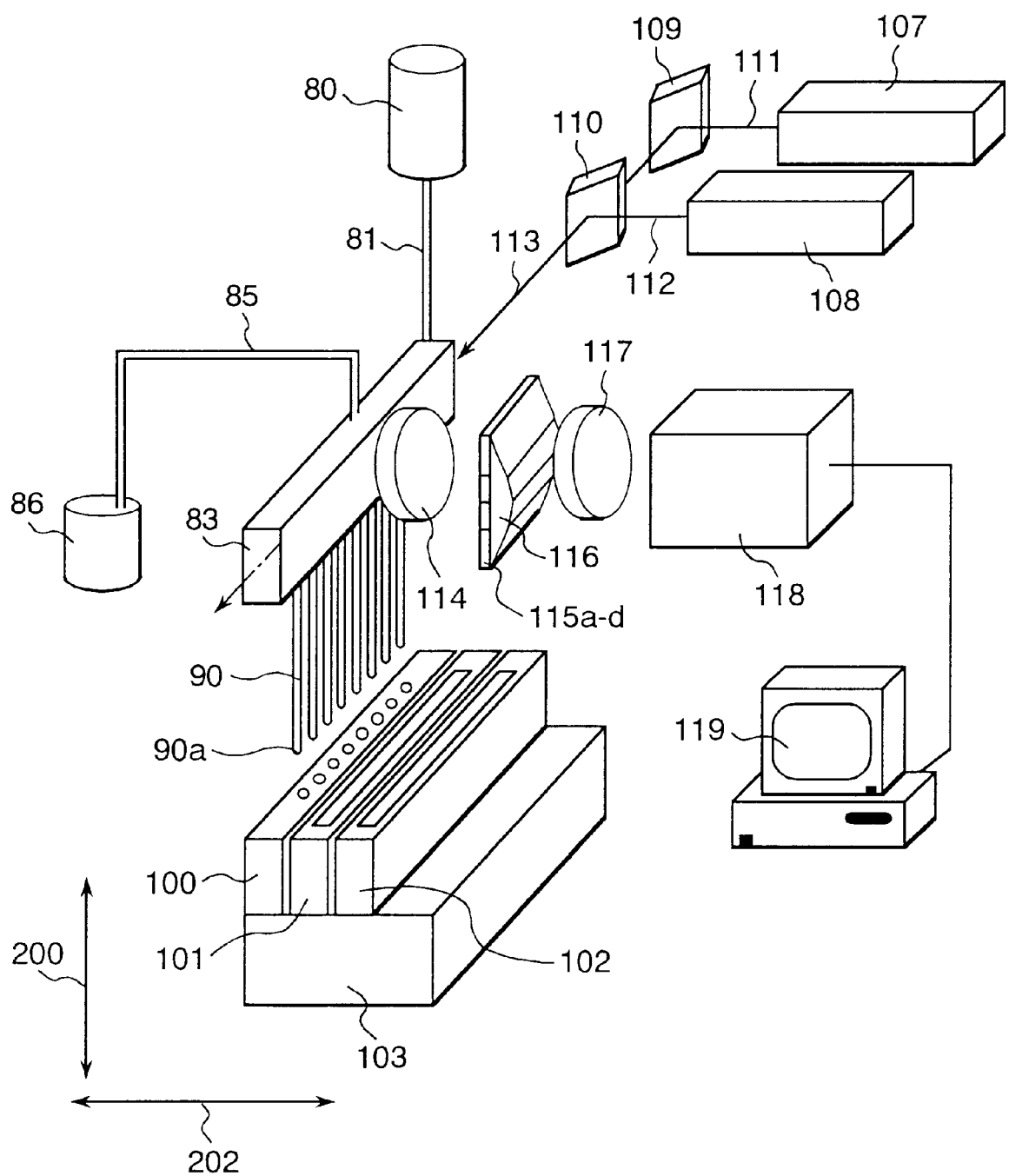
FIG. 2 is a diagram showing the construction of an electrophoresis apparatus using the capillary array shown in FIG. 1.

FIG. 2 is a diagram illustrating the construction of an electrophoresis apparatus using the capillary array shown in FIG. 1. The capillary holder 92, the capillaries 90, the capillary holder 91, the sheath flow cell 83, and the like are arranged in the plane, arranged vertically and fixed so that the sheath flow cell 83 is positioned in the upper part and the buffer solution flows from the lower part to the upper part in the sheath flow cell 83. Below the capillaries 90, a sample vessel 100 having 48 wells formed at the same intervals as those of the capillary ends 90a arranged in a line (each well is filled with the sample solution to be measured), an electrode vessel 101 filled with the buffer solution, and a washing vessel 102 filled with washing solution are arranged, which are moved in the vertical direction 200 and the lateral direction 202 (the direction in which the sample vessel 100, the electrode vessel 101, and the washing vessel 102 are arranged, that is, the direction which perpendicularly crosses a plane formed by the plurality of capillaries 90) by a moving stage 103. Consequently, the capillary ends 90a can be inserted into the sample solution, the buffer solution, and the washing solution in accordance with an object (a movement driving system for the moving stage 103 is omitted in FIG. 2).

The sample solutions for measurement are injected into the 48 wells of the sample vessel 100 by using a pipet. The buffer solution is injected into the electrode vessel 101 and distilled water is injected as the washing solution into the washing vessel 102. First, the moving stage 103 is moved by the movement driving system (the system is omitted in FIG. 2) so that the capillary ends 90a are positioned above the washing vessel 102 and are soaked in the washing solution in the washing vessel 102 by raising the moving stage 103 to wash out dusts, buffer solution, and the like which may be adhered to the capillary ends 90a. Subsequently, the moving stage 103 is lowered and moved by the movement driving system so that the capillary ends 90a are positioned above the sample vessel 100. The moving stage 103 is raised so that the sample solution in the sample vessel 100 comes into contact with the capillary ends 90a, a voltage of −500V is applied to the sample solution side so that an electric field strength is 25V/cm and a voltage of 0V is applied to the buffer solution side in the sheath flow cell 83 and the sample is injected into the capillary ends 90a.

The positive and negative electrodes and a high voltage power source are omitted in FIG. 2. Platinum electrodes arranged for the respective 48 wells of the sample vessel 100 serve as the negative electrodes. The holder 84 is made of stainless steel. Either the holder 84 itself, a platinum electrode arranged in the upper part of the sheath flow cell 83, or a platinum electrode arranged in the drain vessel 86 is used as the positive electrode.

After injecting the samples into the capillary ends 90a, the moving stage 103 is moved by the movement driving system, and the capillary ends 90a are moved into the electrode vessel 101 and are soaked into the buffer solution. A voltage is applied to the platinum electrodes held in the buffer solution in the electrode vessel 101. Various values can be used for the voltage to apply. In this case, a voltage of −500V such that the electric field strength is 25V/cm is applied for first five minutes. Subsequently, a voltage of −2000V such that the electric field strength is 100V/cm is applied. As a result of the electrophoresis, the DNA fragment is separated every molecular weight and eluted from the capillary ends 90b into the sheath flow cell. The eluted DNA fragments are fluorescence measured.

Since the sheath flow is formed near the capillary ends 90b, the DNA fragments eluted from the capillary ends 90b flow without being mixed. Consequently, the fluorescence measurement can be executed by simultaneously injecting 48 samples into the capillaries, respectively, and simultaneously performing the electrophoresis. With respect to the injection of the samples, if the sample vessel 100 is preliminarily filled with sample solutions, electric field injection can be performed. Therefore, unlike a conventional case of using slab gel, it is unnecessary to manually inject samples into gels one by one by pipetting. The operability can be consequently improved.

The fluorescent measurement method will be described hereinbelow. As a light source for exciting the fluorophore labelling the sample, two kinds of laser units (an Argon laser unit 108 for emitting laser light having the wavelength of 488 nm and a YAG laser unit 107 for emitting laser light having the wavelength of 532 nm) are used. An Argon laser beam 112 and a YAG laser beam 111 are made coaxial by a mirror 109 and a dichroic mirror 110 and are emitted as one laser beam 113 which is condensed by a lens (not shown) having the focal distance of about 80 mm to the sheath flow cell 83. The fluorescent light generated from the fluorophore passes through a light collecting lens 114, four kinds of spectroscopic filters 115a to 115d, an image splitting prism 116, and an image forming lens 117 and an image is formed on a two-dimensional detector 118. The intensity of fluorophore from the DNA fragments of each sample is measured, change with time is analyzed by a data processing unit 119, and the base sequence of the sample is determined.

Figure 3:
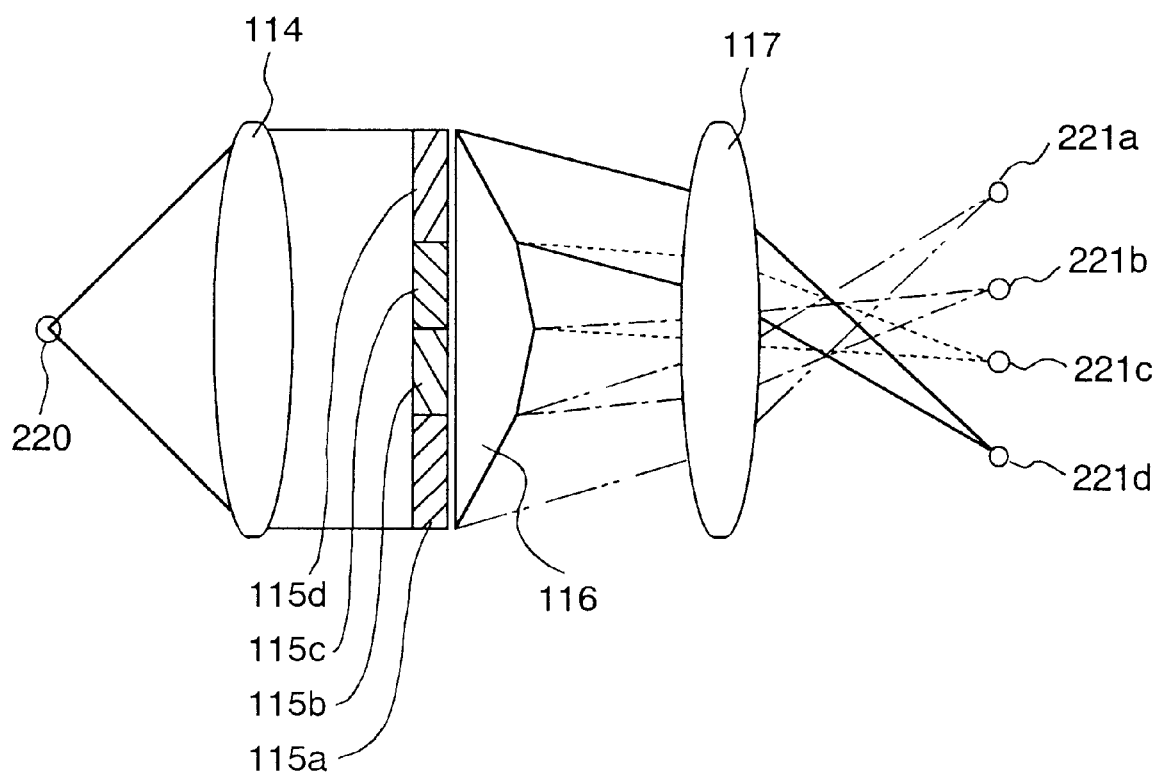
FIG. 3 is a diagram illustrating the construction of an image splitting fluorescent detecting unit in the first embodiment of the invention.

The detection of the fluorescent image will be described with reference to FIG. 3 showing the construction of an image splitting fluorescence detection unit. Fluorescent light emitted from an emitting point 220 of fluorescent light is condensed by the light collecting lens 114, split into four parts by the image splitting prism 116, and images (221a to 221d) are formed by the image forming lens 117. In this case, by arranging the four spectroscopic filters 115a to 115d on the front or rear face of the image splitting prism 116, each split light has a different wavelength component. Although description has been given regarding one emitting point 220 of fluorescent light in FIG. 3, it is similar with respect to all of emitting points of fluorescent light. In the above-mentioned detection of the fluorescent image, the fluorescent light is not detected time-sharedly like in a case of performing the fluorescent detection by laser beam scan or mechanical scan, so that the measurement intervals of the fluorescent intensities are not long and the measurement can be continuously performed in a real time manner with high speed. Since the light collecting lens is arranged in front of the image splitting prism, the fluorescent light collecting efficiency is improved and detection sensitivity is improved. A cylindrical lens can be also used in place of the light collecting lens. Since only light in one direction is collected, although the efficient is about the half of that in a case of using a regular convex lens, the detection sensitivity can be largely improved as compared with a case of not using the convex lens.

In case of using the image splitting prism, when the position of the emitting point of the fluorescent light is deviated, the ratio of intensity of the image to be split largely fluctuates. In case of using the slab gel, there is a problem such that the light path of the laser light entering the gel is curved by heat generation of the gel or the like, the position of the emitting point of the fluorescent light is deviated, and the measurement accuracy tends to deteriorate. According to the embodiment, however, since the laser light passes through aqueous solution, the laser light is not curved and a predetermined position is irradiated with the laser light. Thus, the measurement accuracy is improved as compared with the conventional technique.

According to the embodiment, since black is used for the color of coating of the capillary, even if scattered light or reflected light of the laser light is emitted to the capillary, the capillary hardly fluoresces. Consequently, the background light intensity is not increased and the high sensitive detection can be performed. By adjusting the four kinds of spectroscopic filters 115a to 115d so as to transmit the fluorescent light from the fluorophores FA, FC, FG, and FT, the A, C, G, and T fragment groups can be identified and measured. In reality, however, the emission wave lengths from the fluorophores FA, FC, FG, and FT are overlapped with each other. The overlap is corrected and electropherogram of each of the fluorophores FA, FC, FG, and FT is obtained. The electropherogram gives migration spectrum of each of the A, C, G, and T fragments and the DNA base sequence can be determined by a regular method.

The laser light 113 is focused by the lens. Since the lens of the focal distance of about 80 mm is used, all the migration lanes (about 20 mm in the embodiment) are uniformly irradiated with the laser light. Various modifications which will be described hereinbelow can be derived from the embodiment. Although the laser beams can be emitted non-coaxially, however, when the laser beams are coaxially emitted, since the same position is irradiated with the two laser beams, migration lengths of the DNA fragments excited by the laser beams become constant. Consequently, migration time is not deviated and the analyzing accuracy is improved. In case of the fluorophores absorbed by both of the laser beams having different wavelengths, when the laser beams are coaxially emitted, the excitation light intensity is increased, so that the analyzing accuracy is improved. The measurement can be also performed by only one kind of laser beam. Further, in case of using laser beams of two kinds of wavelengths, the laser beams may be emitted so as to parallelly deviate from each other. For example, when the wavelength of Raman scattering of the laser light of water by the Ar laser light is close to a wavelength of fluororescent light from a fluorophore which can be excited by laser light having another wavelength, the intensity of Raman scattering of the laser light of water becomes noise and the measurement sensitivity deteriorates. However, the laser beams of two kinds of wavelengths are deviated in parallel, and the intensity of fluorescent light is measured at different positions, the influence by the intensity of Raman scatter can be prevented.

The migration conditions (migration voltage, time, gel concentration), the number of capillaries, the length and the thickness of a capillary, the intervals of the upper and lower ends of capillaries in the capillary array, the shape of the sample vessel (the number and intervals of wells and material are included) and the like of the embodiment can be variably changed. Further, the apparatus of the embodiment can be used not only for the DNA base sequencing but also for general detection and diagnosis of DNA fragments. In the fluorescent light detection, it is also possible that the image splitting prism is not used, only one color (one kind) of the spectroscopic filter is used, and the fluorescent light from a fluorophore of one kind can be measured. The irradiation method of laser light is not limited to the embodiment. An irradiation method of scanning laser light and a method of irradiating the laser light to a range wider than the width of the capillary array are also possible. Laser light and a photomultiplier are simultaneously used and the laser light can be scanned.

According to the embodiment, since all of the capillaries are arranged on the same plane at least in an analyzing region, all of them can be caught by a heated and/or cooled panel in a plane shape so that the temperature can be easily adjusted. The temperature of the most part (90% or more) in the longitudinal direction of the capillary can be adjusted. Since the capillary can be used almost vertically, the total length of the capillary can be shortened, a load of bending or the like is not given to the gel prepared in the capillary and it is consequently unnecessary to consider the possibility that the resolution of the gel deteriorates.

The total length of the capillary can be made 10 cm or shorter, so that the sample can be measured at high speed. Further, since the buffer solution flows from the lower part to the upper part, when bubbles occur in the sheath flow for some reason, the bubbles easily escape from the upper part. Even in the case where a large dust heavier than water is mixed in the buffer solution, it sinks to the lower part of the cell. Consequently, dusts or the like are not carried by the flow of the buffer solution so that the laser light is not disturbed and the measurement is stable.

Second Embodiment

Figure 4:
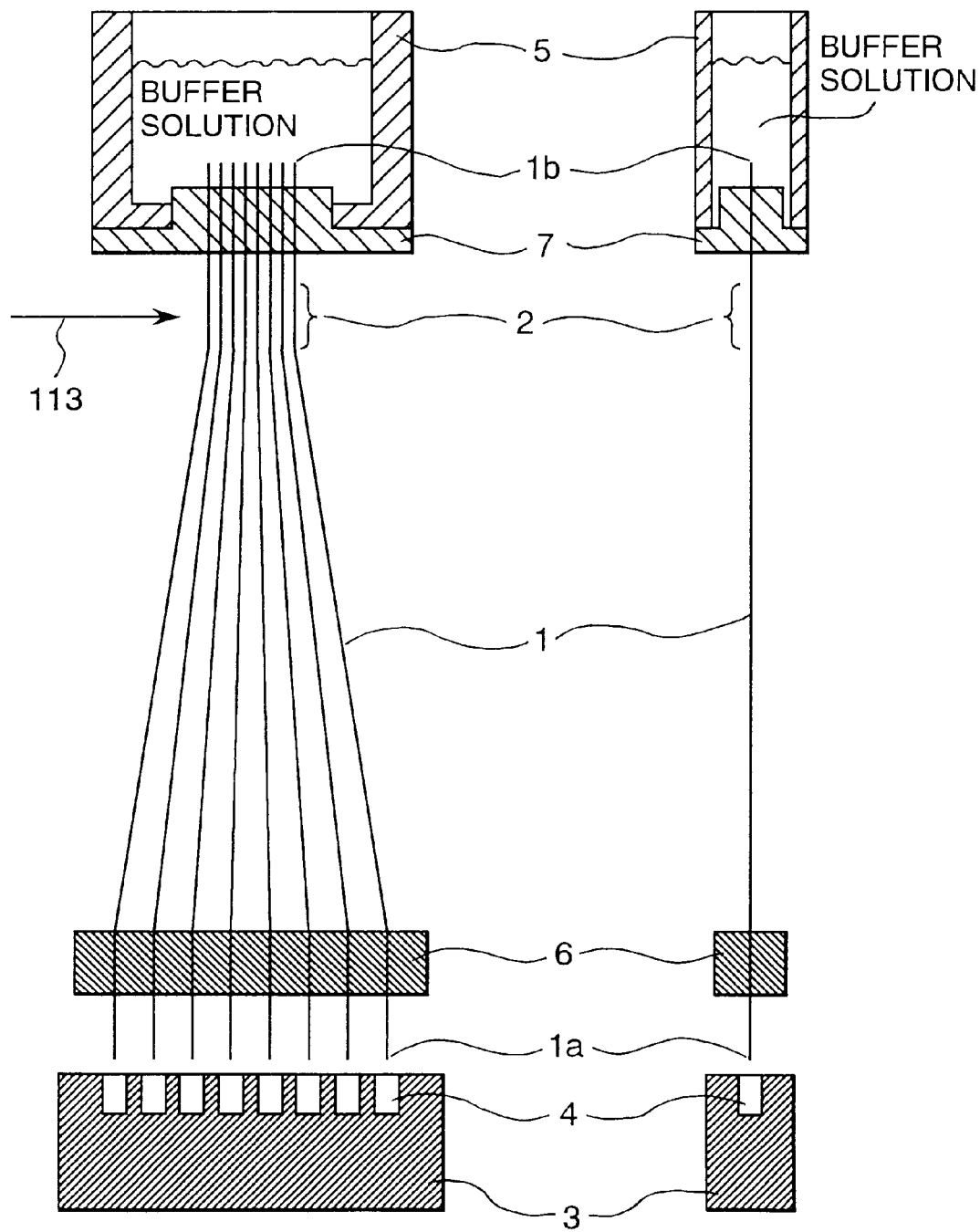
FIG. 4 is cross sections from two directions which perpendicularly cross with each other, showing the schematic construction of a capillary array and an electrophoresis unit according to a second embodiment of the invention.

An electrophoresis apparatus according to a second embodiment having a construction in which a capillary array filled with gel is used will be described. FIG. 4 is cross sections from two directions which perpendicularly cross each other showing a schematic construction of the capillary array and the electrophoresis unit according to the second embodiment. A capillary array in which eight capillaries filled with gel are used and one ends are arranged in a straight line is produced. Although various inner and outer diameters can be used for the capillary, for example, capillaries each having the inner diameter of 0.075 mm, the outer diameter of 0.2 mm, and the length of about 20 cm are used, and in a manner similar to the first embodiment, the capillaries are filled with polyacrylamide gel according to a known method and are used. A window for measuring fluorescent light is preliminarily formed in a position of about 15 cm from the sample injection end of each capillary. The window is formed in a manner such that either a region of about 3 mm to 5 mm for transmitting the laser light and a region for detecting the fluorescent light, or the whole circumference of the polyimide coating of the capillary is removed. The fluorescent light is detected by irradiating the window with the laser light (on-column measurement). That is, windows of a plurality of capillaries are irradiated with the laser light.

On capillary holders 6, 7, attaching grooves at intervals of 3 mm and 0.2 mm are formed, respectively, in order to uniform the intervals of the capillaries and facilitate attachment of the capillary array or the like. First, eight capillaries 1 are arranged on the same plane so that windows 2 for fluorophore measurement are lined, and the capillaries 1 are fixed to the capillary holders 6, 7. One ends of the capillaries are arranged at the intervals of 3 mm and the other ends are arranged at the intervals of 0.2 mm and the respective ends are cut so as to be almost aligned. Capillary ends 1a fixed at the intervals of 3 mm are ends on the sample injecting side and capillary ends 1b on the opposite side are sample eluting ends in which separated sample fragments are eluted.

The capillary holder 6, the capillaries 1, the capillary holder 7, and the like are arranged in the plane. The capillary holder 7 is attached to the lower part of an electrode vessel 5 and the capillary array is vertically fixed. Below the capillaries 1, a sample vessel 3 having eight wells in a line formed at the same intervals as those of the capillary ends 1a (each well 4 is filled with a sample solution to be measured) and an electrode vessel (not shown) filled with the buffer solution, and the like are fixed to a moving stage in a manner similar to the first embodiment and operation similar to that of the first embodiment is performed. In a manner similar to the first embodiment, when samples are injected into the wells 4 and a voltage is applied, the samples migrate vertically upward from the lower part toward the electrode vessel 5, subjected to the fluorescent measurement through the windows 2 for fluorescent measurement, and fragments are eluted from the capillary ends 1b to the solution in the electrode vessel 5.

In the fluorescent measurement, in a manner similar to the first embodiment, the laser light is emitted and the fluorescent light is detected. Although the sheath flow cell 83 shown in FIG. 2 is irradiated with the laser light in the first embodiment, in the second embodiment, the plurality of capillaries arranged in the plane are irradiated with the laser light 113 shown in FIG. 2 through the windows of the capillaries. The fluorescent measurement is performed through the windows of the plurality of capillaries by using the fluorescent measurement system shown in FIG. 2 or various fluorescent measurement systems described in the first embodiment. As for the laser light irradiation method, various methods described in the first embodiment can be also used. Since all of the capillaries are arranged in the same plane in the second embodiment, similar effects as those of the first embodiment can be obtained.

Third Embodiment

Figure 5:
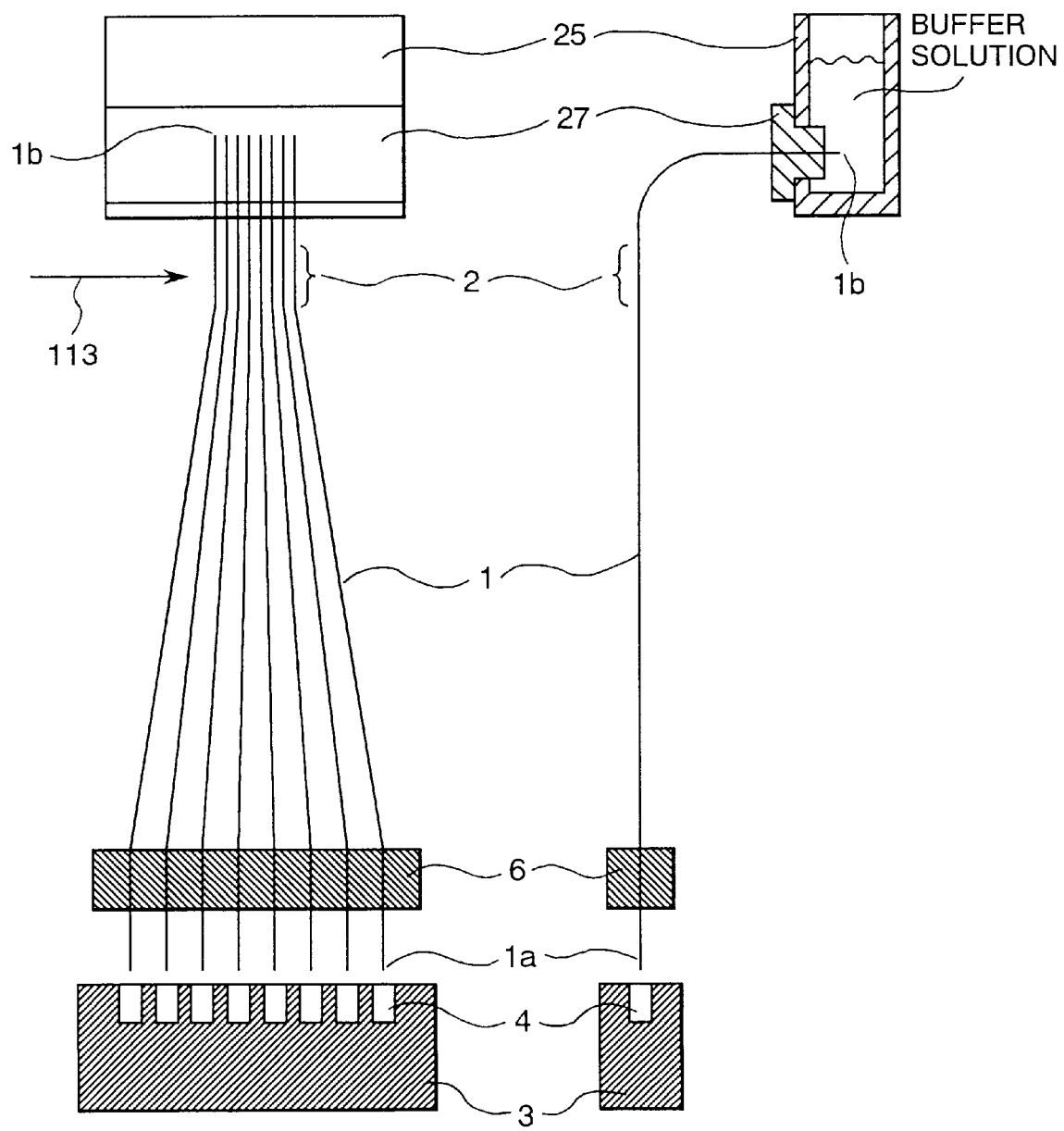
FIG. 5 is front and side views including a partial section showing schematic constructions of a capillary array and an electrophoresis unit according to a third embodiment of the invention.

An electrophoresis apparatus according to a third embodiment having a construction in which a capillary array filled with gel is used will be described. FIG. 5 is front and side views including a partial section showing a schematic construction of the capillary array and the electrophoresis unit according to the third embodiment. Although the capillary holder 7 is connected to the lower part of the electrode vessel 5 in the second embodiment, according to the third embodiment, a capillary holder 27 is connected to a side face of an electrode vessel 25 as shown in FIG. 5. In FIG. 5, the same constructions and dimensions as those shown in FIG. 4 are designated by the same reference numerals. That is, the window for fluorescent measurement is opened in the position of about 15 cm from the sample injecting end 1a of each of the capillaries 1. The capillaries 1 are arranged vertically so that the parts from the capillary ends 1a to the windows for fluorescent measurement are on the same plane. Then, the capillaries 1 are bent and the capillary holder 27 is attached to the lower part of the side face of the electrode vessel 25 together with the capillary ends 1b and is fixed.

In a manner similar to the first and second embodiments, samples are injected into the wells 4. When a voltage is applied, the samples migrate vertically from the lower part toward the electrode vessel 25 and are fluorescent measured through the windows 2 for fluorescent measurement. After that, the moving direction is curved at 90 degrees and fragments are eluted from the capillary ends 1b into the solution in the electrode vessel 25. In a manner similar to the first embodiment and modifications, the laser light is emitted and the fluorescent detection is performed. In the third embodiment as well, since the parts from the sample injecting ends to the fluorescent measurement positions of all of the capillaries are arranged in the same plane, effects similar to those of the first embodiment can be obtained.

Although polyacrylamide gel has been described as a migration medium to be filled in the capillaries in above mentioned embodiments, it will be obviously understood that other gel or polymer can be also filled.

What is claimed is:

1. A capillary electrophoresis apparatus comprising:
a plurality of capillaries, filled with a migration medium, each having a first end into which a sample is injected and a second end from which a component included in the sample is eluted;
a sheath flow cell in which the second ends are arranged in a straight line at first predetermined intervals and terminated;
means for flowing a buffer solution in the sheath flow cell from the lower part of the sheath flow cell to the upper part of the sheath flow cell; and
means for detecting a component eluted from each of the capillaries in the sheath flow cell near the second ends.

2. An apparatus according to claim 1, wherein the capillaries are arranged in substantially the same plane.

3. An apparatus according to claim 1, further comprising a plurality of capillaries or rod members, each having an outer shape of substantially the same size as the capillaries filled with a migration medium, arranged at the first predetermined intervals on both sides of an array of the second ends.

4. An apparatus according to claim 1, wherein the migration medium includes either a gel or a polymer.

5. An apparatus according to claim 1, wherein the first ends are arranged lower than the second ends.

6. An apparatus according to claim 1, wherein the first ends are arranged in a straight line at second predetermined intervals; and
wherein the apparatus further comprises a sample vessel having a plurality of wells which respectively contain a plurality of samples, the sample wells being arranged in a straight line at the second predetermined intervals at which the first ends are arranged in parallel to an array of the first ends.

7. An apparatus according to claim 1, wherein the first ends are arranged in a straight line at second predetermined intervals; and
wherein the apparatus further comprises:
a sample vessel having a plurality of wells which respectively contain a plurality of samples, the wells being arranged in a straight line at the second predetermined intervals at which the first ends are arranged in parallel to an array of the first ends; and
means for moving the sample vessel.

8. An apparatus according to claim 1, wherein the capillaries have a black coating at least near the second ends.

9. A capillary electrophoresis apparatus comprising:
a plurality of capillaries, filled with a migration medium, each having a first end into which a sample is injected and a second end from which a component included in the sample is eluted;
a sheath flow cell in which the second ends are arranged in a straight line at first predetermined intervals and terminated, and a sheath flow is formed;
a buffer solution vessel for containing a buffer solution, the buffer solution vessel being connected by a conduit to a lower part of the sheath flow cell;
a drain vessel connected by a conduit to an upper part of the sheath flow cell;
means for causing the buffer solution to flow from the buffer solution vessel through the sheath flow cell into the drain vessel, thereby forming the sheath flow in the sheath flow cell;
an optical system for emitting laser light along the straight line near the second ends; and
a fluorescence detection system for detecting fluorescent light generated from a fluorophore labelling a component included in the sample eluted from each of the second ends.

10. An apparatus according to claim 9, wherein the liquid level of the buffer solution contained in the buffer solution vessel is higher than the liquid level of the buffer solution contained in the drain vessel.

11. An apparatus according to claim 9, wherein the capillaries are arranged in substantially the same plane.

12. An apparatus according to claim 9, wherein the migration medium includes either a gel or a polymer.

13. An apparatus according to claim 9, wherein the first ends are arranged in a straight line at second predetermined intervals; and
wherein the apparatus further comprises a sample vessel having a plurality of wells which respectively contain a plurality of samples, the wells being arranged in a straight line at the second predetermined intervals at which the first ends are arranged in parallel to an array of the first ends.

14. A capillary electrophoresis apparatus comprising:
a plurality of capillaries, filled with a migration medium, each having a first end into which a sample is injected and a second end from which a component included in the sample is eluted;
a sheath flow cell in which the second ends are arranged in a straight line at first predetermined intervals and terminated, and a sheath flow is formed;
a buffer solution vessel for containing a buffer solution which flows into the sheath flow cell;
a drain vessel for containing the buffer solution when the buffer solution flows out of the sheath flow cell;
an optical system for emitting laser light along the straight line near the second ends; and
a fluorescence detection system for detecting fluorescent light generated from a fluorophore labelling a component included in the sample eluted from each of the second ends;
wherein the buffer solution flows in the sheath flow cell from the lower part of the sheath flow cell to the upper part of the sheath flow cell, thereby forming the sheath flow in the sheath flow cell; and
wherein the apparatus further comprises a plurality of capillaries or rod members, each having an outer shape of substantially the same size as the capillaries filled with a migration medium, arranged at the first predetermined intervals on both sides of an array of the second ends.

15. A capillary electrophoresis apparatus comprising:
a plurality of capillaries, filled with a migration medium, each having a first end into which a sample is injected and a second end from which a component included in the sample is eluted;
a sheath flow cell in which the second ends are arranged in a straight line at first predetermined intervals and terminated, and a sheath flow is formed;
a buffer solution vessel for containing a buffer solution which flows into the sheath flow cell;
a drain vessel for containing the buffer solution when the buffer solution flows out of the sheath flow cell;
an optical system for emitting laser light along the straight line near the second ends; and
a fluorescence detection system for detecting fluorescent light generated from a fluorophore labelling a component included in the sample eluted from each of the second ends;

wherein the buffer solution flows in the sheath flow cell from the lower part of the sheath flow cell to the upper part of the sheath flow cell, thereby forming the sheath flow in the sheath flow cell; and wherein the first ends are arranged lower than the second ends.

16. A capillary electrophoresis apparatus comprising:

a plurality of capillaries, filled with a migration medium, each having a first end into which a sample is injected and a second end from which a component included in the sample is eluted;

a sheath flow cell in which the second ends are arranged in a straight line at first predetermined intervals and terminated, and a sheath flow is formed;

a buffer solution vessel for containing a buffer solution which flows into the sheath flow cell;

a drain vessel for containing the buffer solution when the buffer solution flows out of the sheath flow cell;

an optical system for emitting laser light along the straight line near the second ends; and a fluorescence detection system for detecting fluorescent light generated from a fluorophore labelling a component included in the sample eluted from each of the second ends;

wherein the buffer solution flows in the sheath flow cell from the lower part of the sheath flow cell to the upper part of the sheath flow cell, thereby forming the sheath flow in the sheath flow cell;

wherein the first ends are arranged in a straight line at second predetermined intervals; and wherein the apparatus further comprises:
  a sample vessel having a plurality of wells which respectively contain a plurality of samples, the wells being arranged in a straight line at the second predetermined intervals at which the first ends are arranged in parallel to an array of the first ends; and
  a moving stage for moving the sample vessel.

17. A capillary electrophoresis apparatus comprising:

a plurality of capillaries, filled with a migration medium, each having a first end into which a sample is injected and a second end from which a component included in the sample is eluted;

a sheath flow cell in which the second ends are arranged in a straight line at first predetermined intervals and terminated, and a sheath flow is formed;

a buffer solution vessel for containing a buffer solution which flows into the sheath flow cell;

a drain vessel for containing the buffer solution when the buffer solution flows out of the sheath flow cell;

an optical system for emitting laser light along the straight line near the second ends; and a fluorescence detection system for detecting fluorescent light generated from a fluorophore labelling a component included in the sample eluted from each of the second ends;

wherein the buffer solution flows in the sheath flow cell from the lower part of the sheath flow cell to the upper part of the sheath flow cell, thereby forming the sheath flow in the sheath flow cell; and wherein the capillaries have a black coating at least near the second ends.

18. A capillary electrophoresis apparatus comprising:

a plurality of capillaries each having a first end into which a sample is injected, a second end from which a component included in the sample is eluted, and a light irradiation part which is located between the first end and the second end, the first ends being arranged in a straight line at predetermined intervals;

a light source which irradiates the irradiation parts with laser light;

a sample vessel having a plurality of wells which respectively contain a plurality of samples, the sample wells being arranged in a straight line at the predetermined intervals at which the first ends are arranged in parallel to an array of the first ends; and means for moving the sample vessel relative to the first ends so that the first ends are inserted into the samples contained in the wells;

wherein parts of the capillaries from the first ends to the light irradiation parts are arranged in the same plane; and wherein the first ends are arranged lower than the light irradiation parts and the second ends.

19. A capillary electrophoresis apparatus according to claim 18, wherein the light source irradiates the light irradiation parts with the laser light in a direction parallel to the plane.

* * * * *